United States Patent [19]
Gevins

[11] Patent Number: 5,447,166
[45] Date of Patent: Sep. 5, 1995

[54] NEUROCOGNITIVE ADAPTIVE COMPUTER INTERFACE METHOD AND SYSTEM BASED ON ON-LINE MEASUREMENT OF THE USER'S MENTAL EFFORT

[76] Inventor: Alan S. Gevins, 532 Waller St., San Francisco, Calif. 94117

[21] Appl. No.: 183,621

[22] Filed: Jan. 19, 1994

Related U.S. Application Data

[63] Continuation-in-part of Ser. No. 766,826, Sep. 26, 1991, Pat. No. 5,295,491.

[51] Int. Cl.$^6$ .......................................... A61B 5/0476
[52] U.S. Cl. .................................................. 128/731
[58] Field of Search ................................ 128/731, 732

[56] References Cited

U.S. PATENT DOCUMENTS 740,385  10/1903  Bassell ............................. 128/791
3,901,215  8/1975  John ................................ 128/731
4,913,160  4/1990  John ................................ 128/731
4,987,903  1/1991  Keppel et al. .................. 128/731

Primary Examiner—William E. Kamm
Assistant Examiner—Scott M. Getzow

[57] ABSTRACT

A human-computer interface uses neuroelectric signals recorded from the user's scalp i.e. electroencephalograms (EEGs) to alter the program being run by the computer, for example to present less or more difficult material to the user, depending on the user's neurocognitive on-line workload score. Each user is tested with a standard battery of tasks, while wearing an EEG hat, to calibrate a neurocognitive workload function. The calibrated function is user-specific and is obtained by modifying a neural network pattern analyzer which has been previously trained to index neurocognitive workload using data from a group of subjects performing the same battery of tasks.

30 Claims, 9 Drawing Sheets

NEUROCOGNITIVE ADAPTIVE COMPUTER INTERFACE METHOD AND SYSTEM BASED ON ON-LINE MEASUREMENT OF THE USER'S MENTAL EFFORT

This invention was made with Government Support under contract number F49620-92-C-0013 awarded by the Air Force Office of Scientific Research. The Government has certain rights in this invention.

This application is a continuation-in-part application based in part on application Ser. No. 07/766,826 for "Non-Invasive Human Neurocognitive Performance Testing Method and System", filed Sep. 26, 1991 now U.S. Pat. No. 5,295,491, issued Mar. 22, 1994.

BACKGROUND OF THE INVENTION

1. Field of the Invention

The present invention relates to a human-computer interface using neuroelectric signals recorded from the user's scalp, i.e., electroencephalograms (EEGs).

2. Description of Related Art

Conventional computer user interfaces are driven solely by behavioral responses (i.e. muscle activity) by the user with a keyboard, mouse, joystick, touchscreen, pen or similar device, or a data glove in a virtual reality system. In this type of system, the user receives information from the computer screen and audio system in the form of visual and auditory stimuli, (or haptic stimuli in a virtual reality system), processes them, and makes a deliberate behavioral action which the computer interprets and acts upon. Computers that interpret human speech, or that use devices to determine where the user is looking, are other examples of interfaces that are controlled by behavioral responses from the user. Another type of user interface, which is still in the experimental stage, accepts a user's "thought commands," as measured by EEG signals, to control the movement of a cursor on a display screen.

All these interfaces are intended to allow the user to operate and control the computer system. The computer system has no information about the amounts and types of the user's mental capacities currently being utilizied, or even about the user's state of alertness. This results in a situation in which the overall efficiency of the human-computer system is less than it might be. For example if the user is mentally overloaded, or at the other extreme, if the user is drowsy, the overall performance of the human-computer system will be limited by the ability of the user to process and respond to the information presented by the computer.

Advances in technology have resulted in more complex computer based or computer controlled systems which can overwhelm the user's ability to process and respond to the information presented. Examples of this include jet fighter planes, air traffic control systems, powerplant and factory control systems, emergency management systems, multi-window displays of complex relations in a large data base, securities trading systems, and video games which increase task difficulty beyond a user's ability. New multimedia and virtual reality technologies are likewise expected to produce situations in which a user is mentally overloaded. At the other end of the mental effort continuum, highly automated computer controlled systems can require so little input from the user that the user can become inattentive or drowsy, for example piloting a commercial airliner. Other situations which can cause boredom and resultant inattention or drowsiness include long duration instrument monitoring tasks such as watching radar or sonar displays for unusual activity.

The lack of on-line knowledge of whether the user is mentally underloaded or overloaded is also a major limitation in computer-aided instruction systems. The use of computer-aided instruction is greatly increasing because of its ability to present material at a pace directed by the user, as compared with traditional instruction in which everyone in the class receives the same material at the same rate. However, unlike a human teacher, a computer-aided instruction system has no way of knowing about the user's mental state and therefore can not optimally adapt the material to her or his needs. For example, when a user answers a question incorrectly during a computerized training program, the system does not know whether the user was not paying attention or whether she or he was trying hard and simply did not know or understand the material. In the former case, an alerting signal could be presented and then the same material could be repeated. In the latter case, it would be useful to know whether or not the user was employing an appropriate strategy to solve the problem. If so, a more detailed explanation of the material which was not understood could be presented. If the user was using the wrong strategy for the problem, an explanation of how to go about solving the problem could be presented. For example, it might be determined that at the time the user made an error when answering a question requiring visualization of how the parts of an engine fit together, he was using 75% of his cognitive capacity; visuospatial systems were at 45% of capacity, while verbal encoding and output systems were at 85%. From this information, the system could conclude that the user was trying to solve the problem with a verbal strategy which was not efficient for the problem at hand and could present the user with information showing him or her how to use a visuospatial strategy to solve the problem. There currently is no way to obtain this information except indirectly by querying the user about his or her mental state. Besides distracting from the flow of the instruction session, this approach can be inaccurate since people are not always aware of their mental state.

OBJECTIVES AND FEATURES OF THE INVENTION

Supplemental information provided to the computer about the user's neurocognitive workload could serve to optimize overall human-computer system performance by allowing the computer to adapt the type and quantity of information being presented to match the current mental capacity of the user. In this context, the term "neurocognitive" refers to those mental functions for which physiological indices can be measured. Similarly, the lack of on-line knowledge of whether the user is mentally underloaded or overloaded also limits the capability of computer-aided instruction systems. If the computer could tell that the user was mentally overloaded, it could slow down the presentation of material (less difficult level); or it could speed it up (more difficult level) when the user was underloaded.

What is required in all these situations is a means for the computer system to assess the overall level of the user's mental effort, as well as degree of utilization of major regional brain systems critically involved with perception, cognition, or action, and to use this information to adjust the presentation of information to the user to achieve an optimal level of mental workload. We call this type of computer interface a "Sympathetic Neurocognitive Adaptive Computer Interface". Such an interface would have great utility in computer-aided instruction applications, including multi-media and virtual reality training systems, where knowing the degree and type of mental effort of the user would facilitate the acquisition of new knowledge and skills by allowing the computer system to rapidly adapt the information presented to match the mental capacity of the user. Similarly, in situations where the user is being presented with information but is not required to respond, knowledge about the user's mental workload could be used to adjust the presentation of information. Such an interface could also be used in complex computer controlled systems, such as commercial transportantion and military systems, where the system could take over critical funcions from the user if he/she becomes overloaded or drowsy.

It is an objective of the present invention to provide a method and system for measuring the amount of a person's mental efforts and the degree of utilization of major regional brain systems using neuroelectric (EEG) with or without other physiological signals (e.g., eye, scalp or facial muscle and heart activity) in order to provide the computer system with information about the user's mental workload. These regional brain systems involved with perception, action, and cognition include, but are not limited to: the planum temporale, superior temporal gyrus, Heschl's gyrus and associated structures involved with auditory processing and speech perception; the occipital and inferotemporal cortices and the parieto-occipito-temporal junction and associated structures involved in visual processing and pattern recognition; the precentral gyrus, lateral premotor cortex, supplementary motor cortex, and associated structures involved with the planning, initiation, and execution of motor movements; the dominant hemisphere frontal operculum, dorsalateral frontal cortex, and planum temporale and supramarginal gyrus and associated structures involved with language functions; and the networks of structures encompassing the prefrontal, parietal, and temporal association cortices and associated regions involved in processing spatial information, in preparation and sequential planning, in reasoning, in focusing and shifting attention, in learning, and in working memory.

It is a further objective of the present invention to obtain the metric of mental effort noninvasively and on-line while the user is actively interacting with the computer system or while the user is passively receiving information from the computer.

It is a further objective of the present invention to measure the amount of the user's mental capacity being utilized and the degree of utilization of major regional brain systems so that the computer system can adjust the information it presents to better match the mental workload of the user.

It is still a further objective of the present invention to obtain a user-specific calibration for the metric of mental effort and regional brain systems utilization noninvasively using a combination of stimuli, behavioral tasks, physiological measures and neuroelectric signals to train the computer to recognize the different levels of mental effort and utilization of major regional brain systems for each individual user. The calibration process provides the basis for deriving a user-specific mathematical function for relating patterns of neuroelectric activity, with or without other physiological measures, to overall mental workload level, and to the degree of utilization of specific brain systems involved with a given task or behavior.

It is a feature of the present invention to provide a computer user interface which is sympathetic and responsive to the user's level and type of mental efforts by adapting it's operating parameters (e.g., form, content, speed, etc.) to optimally load the mental capacity and regional brain systems of the user. For example, the computer can speed up or slow down the rate of presentation of a multimedia training session if it determines the user's mental effort is not within an optimal range by comparing the user's current mental effort with the function derived during the calibration process. The computer could further change the distribution of information between visual and auditory modalities, or, for the visual modality, between linguistic and graphical types of information display, to take into consideration the degree of utilization of a user's visual and auditory, or linguistic and graphical brain systems.

It is a further feature of the present invention for the system to present information at the instant at which the user's preparatory attention is optimal as determined by measuring the user's mental effort and regional brain utilization prior to presentation of information and presenting the information only when level of mental effort and regional brain utilization are at appropriate values. Alternatively, the system can change the sense modality or form of the information or alert the user prior to presenting the information if the user's preparatory attention is not optimal as determined by measuring the user's mental effort and regional brain utilization prior to presentation of information.

Other features of the present invention include the ongoing measurement of the user's EEG to determine the degree of utilization of various regional brain areas, and measurement of other physiological signals of scalp and facial muscle, heart and eye activity, using two or more electrodes placed on the body surface. Yet another feature of the present invention is the processing of the neuroelectric and other physiological signals in time intervals ranging from 100 milliseconds to several hours to derive a metric of mental effort which is transmitted to the same or a different computer in order to adjust the operation of the computer or simply to record the user's responses.

SUMMARY OF THE INVENTION

In accordance with the present invention, there is provided a novel method and system for measuring the amount of a person's mental efforts and the degree of utilization of major regional brain systems in order to provide the computer with on-line information about the user's mental workload. These major regional brain systems involved with perception, action, and cognition include, but are not limited to: the planum temporale, superior temporal gyrus, Heschl's gyrus and associated structures involved with auditory processing and speech perception; the occipital and inferotemporal cortices and the parieto-occipito-temporal junction and associated structures involved in visual processing and pattern recognition; the precentral gyrus, lateral premotor cortex, supplementary motor cortex, and associated structures involved with the planning, initiation, and execution of motor movements; the dominant hemisphere frontal operculum, dorsalateral frontal cortex, planum temporale and supramarginal gyrus and associated structures involved with language functions; and the networks of structures encompassing the prefrontal, parietal, and temporal association cortices and associated regions involved in processing spatial information, in preparation and sequential planning, in reasoning, in focusing and shifting attention, in learning, and in working memory. Data concerning the user's mental state is then used by the computer system to optimally adapt the information presented by the computer to match the current mental capacity of the user.

The main advantage of the "Sympathetic Neurocognitive Adaptive Computer Interface" is that it automatically adapts the information presented to the user by taking into consideration the level and type of mental effort the user is expending. This differs from other user interfaces where the system responds only to the user's specific, consciously directed commands.

In order to use the system, it must first be calibrated to the individual user. This is accomplished when the system is first operated by a particular user. After that, an abbreviated calibration is performed at the start of each session or as needed. During the calibration, the user performs a brief battery of standard tasks each with several levels of difficulty while her or his behavioral and physiological data are measured. The tasks, such as those described in patent application Ser. No. 07/766,826, Noninvasive Human Neurocognitive Performance Testing Method and System, now U.S. Pat. No. 5,295,491, are designed to cause the user to make a graded series of efforts to engage basic neurocognitive functions such as working memory, divided attention, spatial and grammatical reasoning, etc. Sensory and motor control tasks are also performed. Then the physiological data are analyzed to form indices characteristic of each difficulty level. The EEG data are further analyzed to form topographic templates to determine the pattern of activation of major regional brain systems for each task. These analyses are used to derive a user-specific mathematical function for relating patterns of neuroelectric activity, with or without other physiological measures, to overall mental workload level, and to the degree of utilization of specific brain systems involved with a given task or behavior. The system then operates as follows: As the user is performing a task at the computer, her or his physiological signals are measured and submitted to the user's personal mathematical mental workload function to determine a score related to the user's overall mental workload level, as well as scores for the relative activation of each of the major regional brain systems. In the case of a user controlling a complex system such as an airplane, the system can take over some of the functions being performed by the user if the overall workload score surpasses a high level theshold. Conversely, if a score is below a low level threshold, the system can assign more functions to the user to perform. The system can also adjust the form of information presented to the user based on the relative activation of the major regional brain systems. For example, if the user's spatial processing areas are too occupied, but the overall mental workload is not too high, the system can change the presentation format of some of the tasks from spatial to numeric and linguistic. In the case of a user performing an attention training exercise, the system can present information at the instant at which the user's preparatory attention is optimal as determined by measuring the user's mental effort and regional brain utilization prior to presentation of information. It can then present the information only when level of mental effort and regional brain utilization are at appropriate values, or it can present information in the sense modality or form for which the user's brain is adequately prepared.

BRIEF DESCRIPTION OF THE DRAWINGS

Other objectives and features of the present invention will be apparent from the following detailed description, taken in conjunction with the accompanying drawings. In the drawings:

FIG. 2A shows such average power spectra for Subject 1; FIG. 2B shows such average power spectra for Subject 2; FIG. 2C shows such average power spectra for Subject 3; and FIG. 2D shows such average power spectra for Subject 4. Each of FIGS. 2A–2D shows such average power spectra in sixteen channels. Spectra averaged over all task trials are shown over each labelled recording site on schematic heads. For all subjects one or more channels exhibit depressed alpha band activity (around 10 Hz) with increased mental workload. With the exception of subject 4, all subjects showed increased beta band and scalp muscle activity (above 13 Hz) with increased workload. Subject 4 showed decreased beta and scalp muscle activity with higher workload.

FIG. 3A shows such error probabilities for Subject 1; FIG. 3B shows such error probabilities for Subject 2; FIG. 3C shows such error probabilities for Subject 3; and FIG. 3D shows such error probabilities for Subject 4.

DETAILED DESCRIPTION OF THE INVENTION

Figure 1:
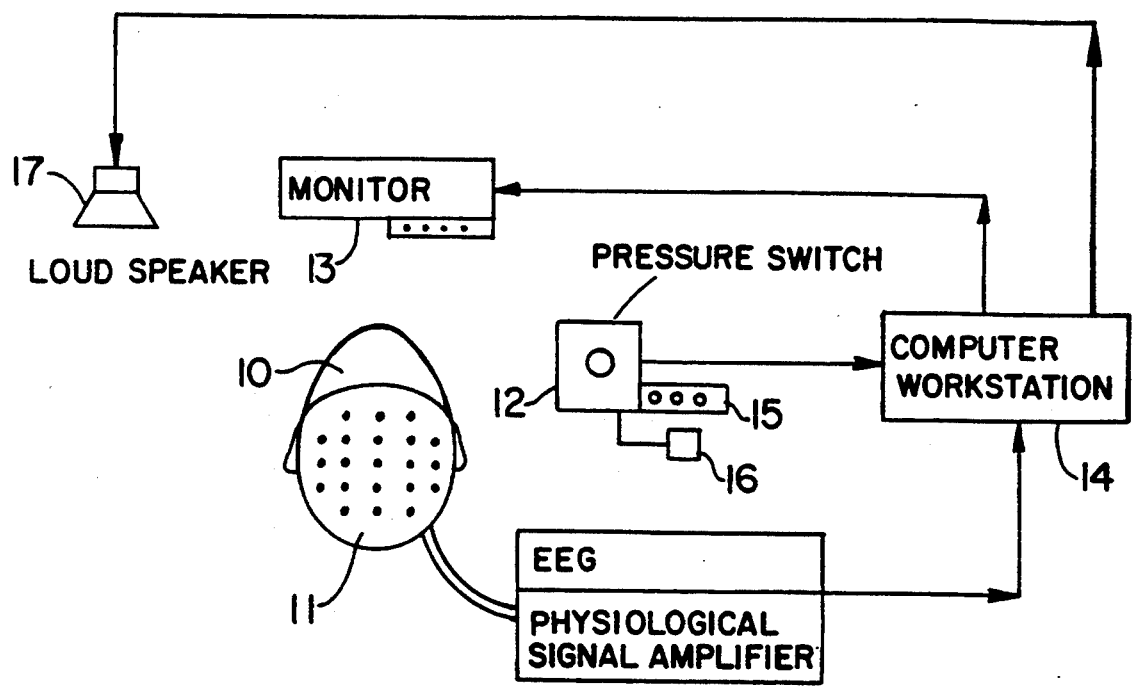
FIG. 1 is a schematic diagram of the system of the current invention.
Figure 2A:
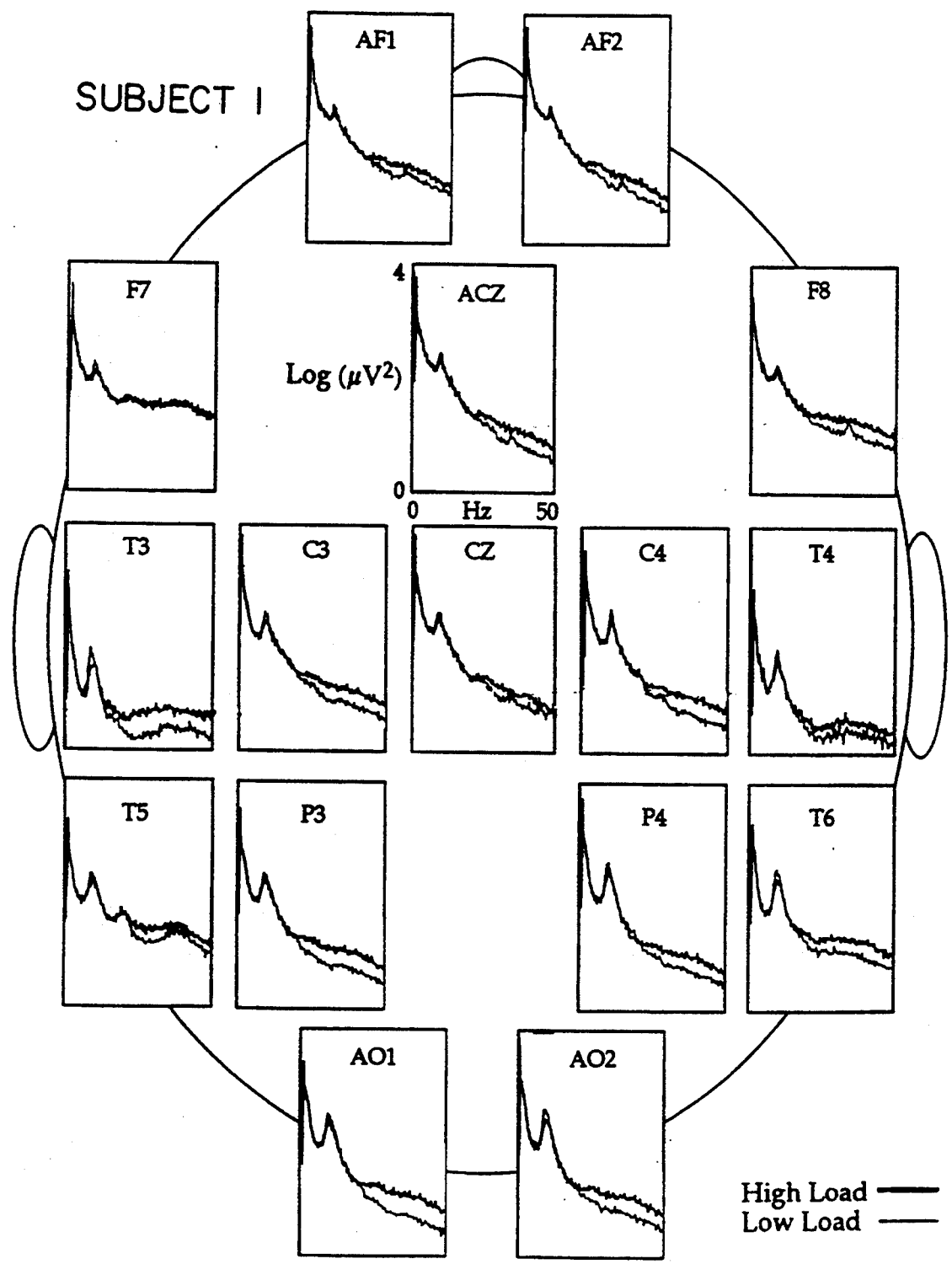
FIG. 2A–2D show the average power spectra of EEG data for the low (thin line) and high (thick line) mental workload conditions from each of four subjects for the 16 EEG channels analyzed.
Figure 2B:
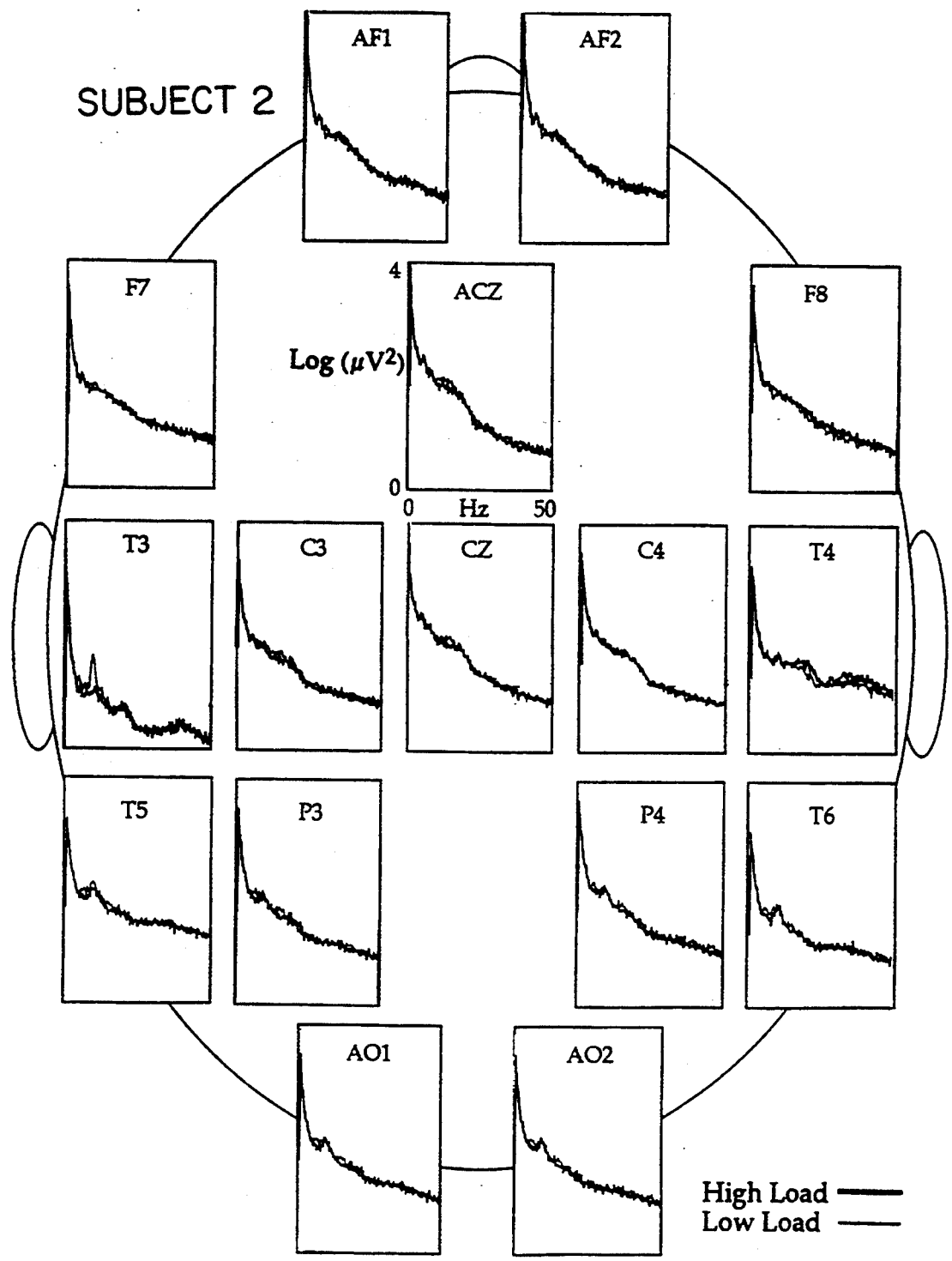
Figure 2C:
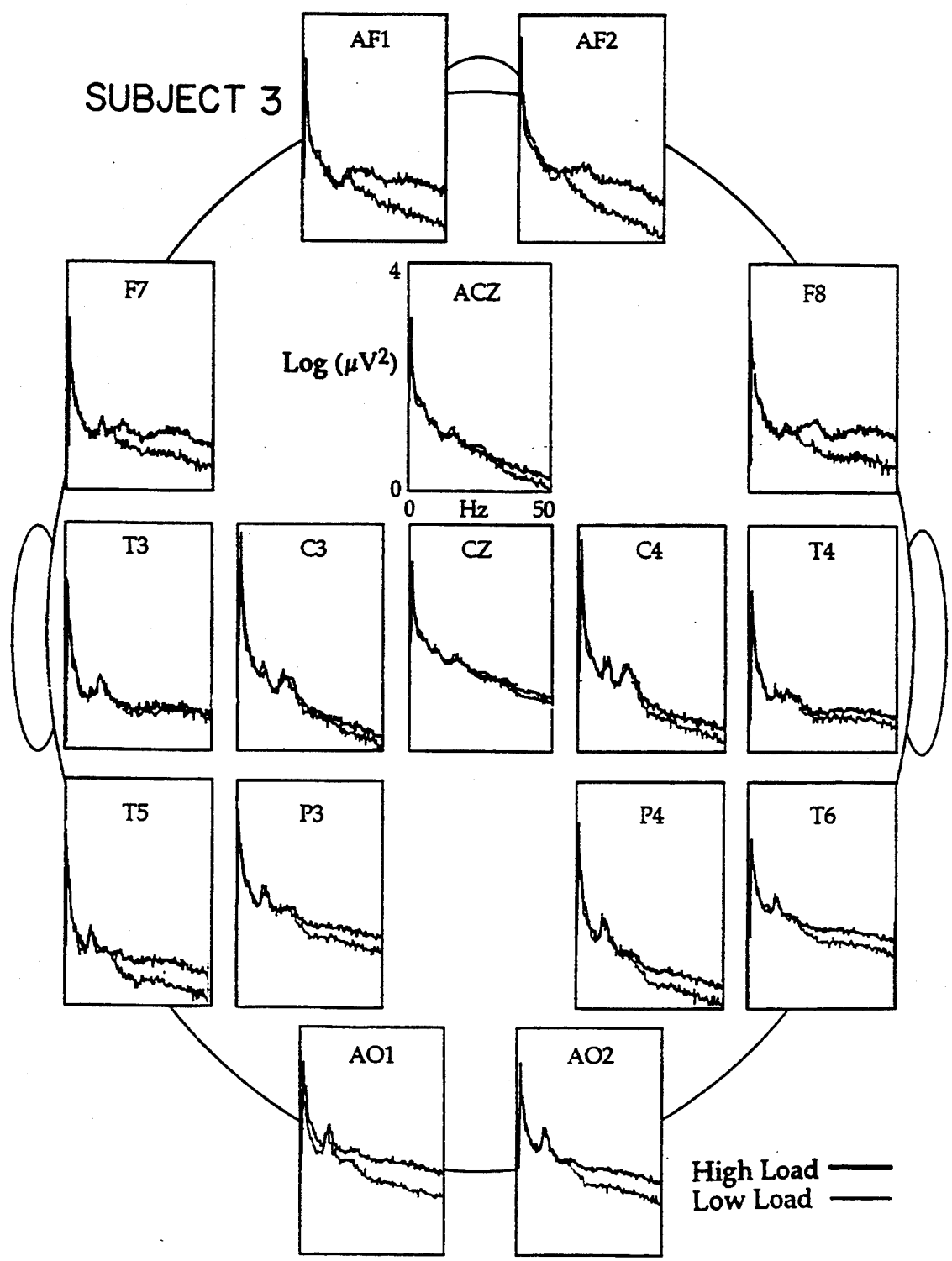
Figure 2D:
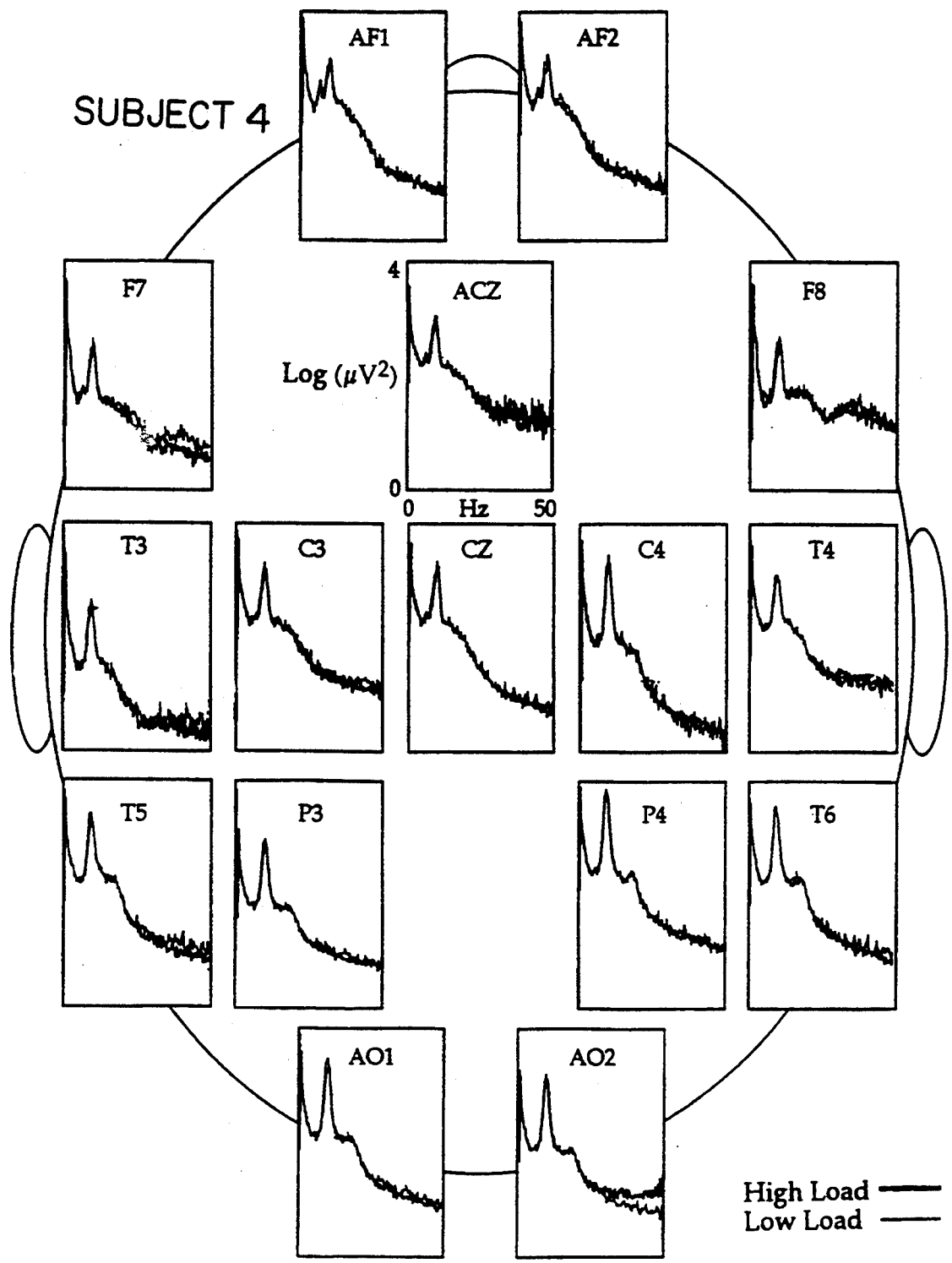
Figure 3A:
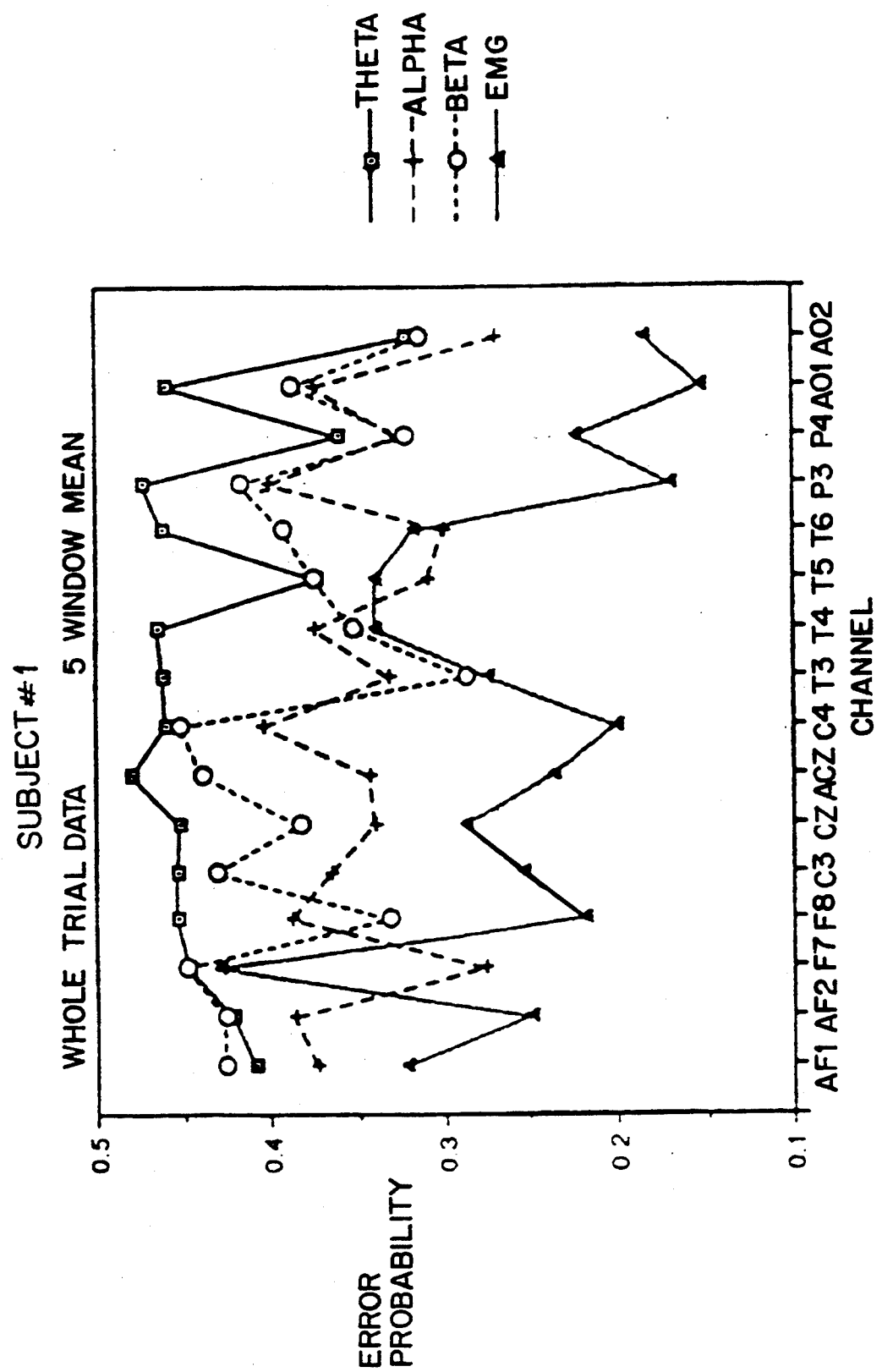
FIGS. 3A–3D: One-dimensional error probabilities for distinguishing low and high mental workload levels for the four frequency bands shown for each of the four subjects.
Figure 3B:
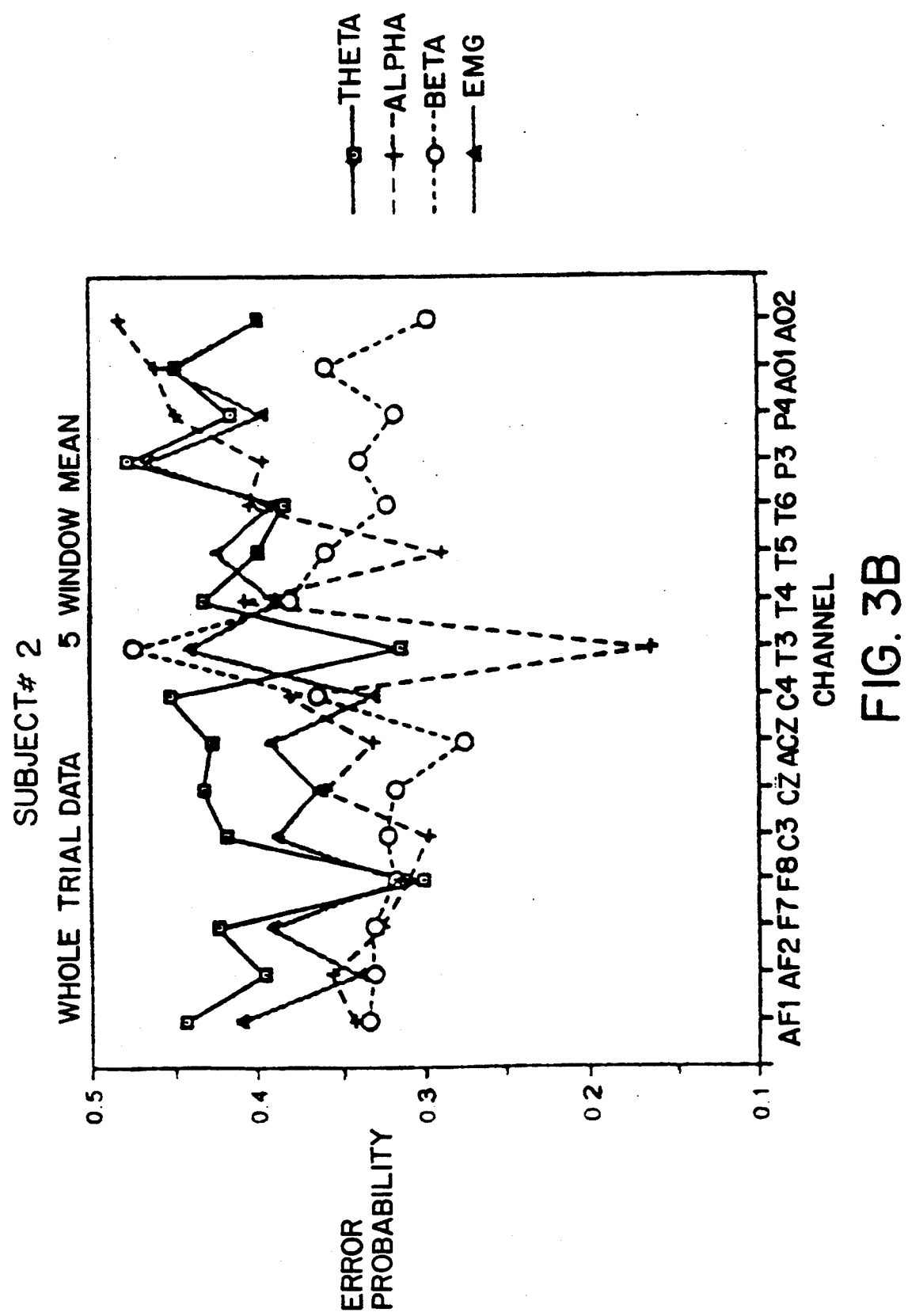
Figure 3C:
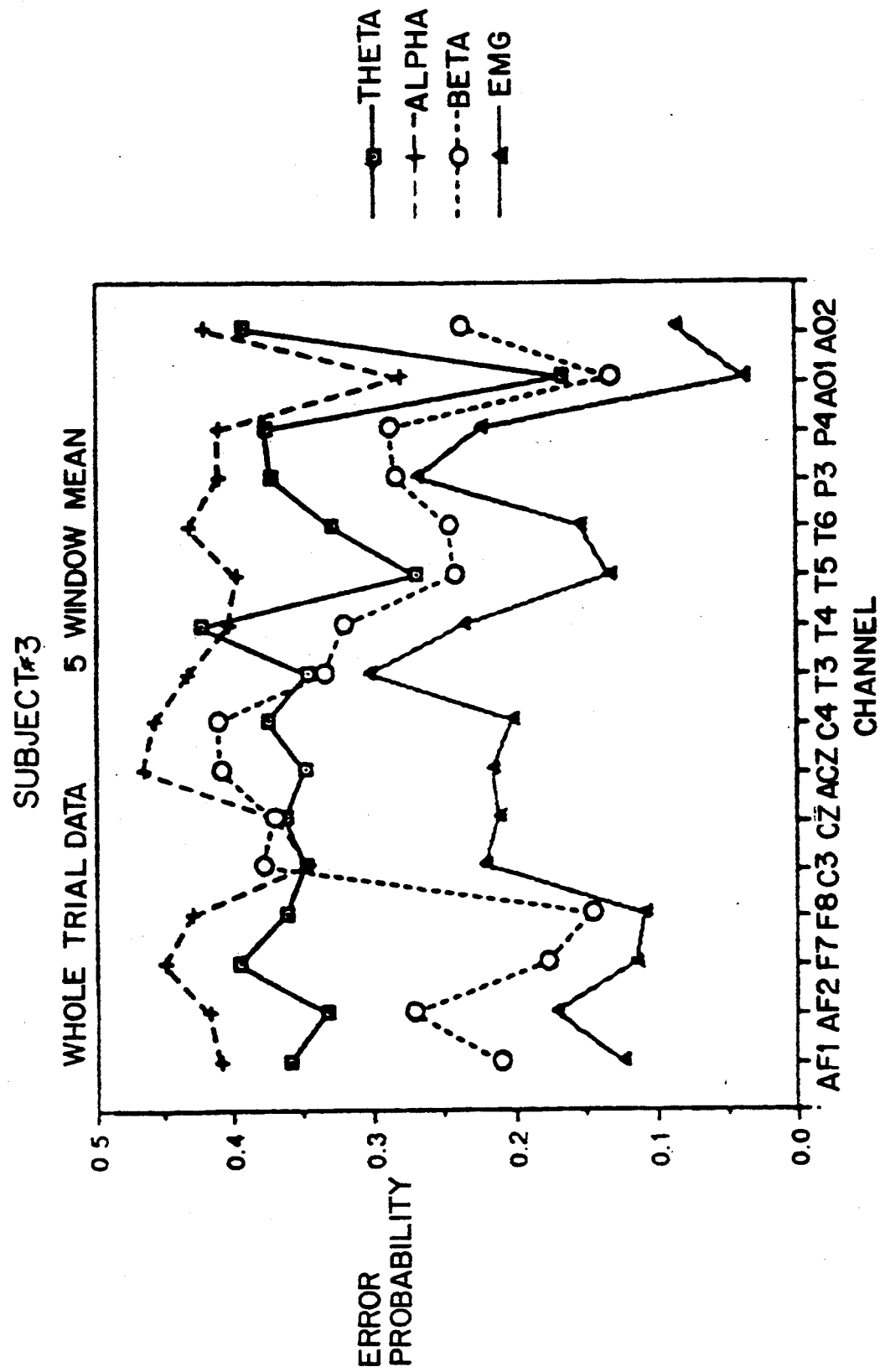
Figure 3D:
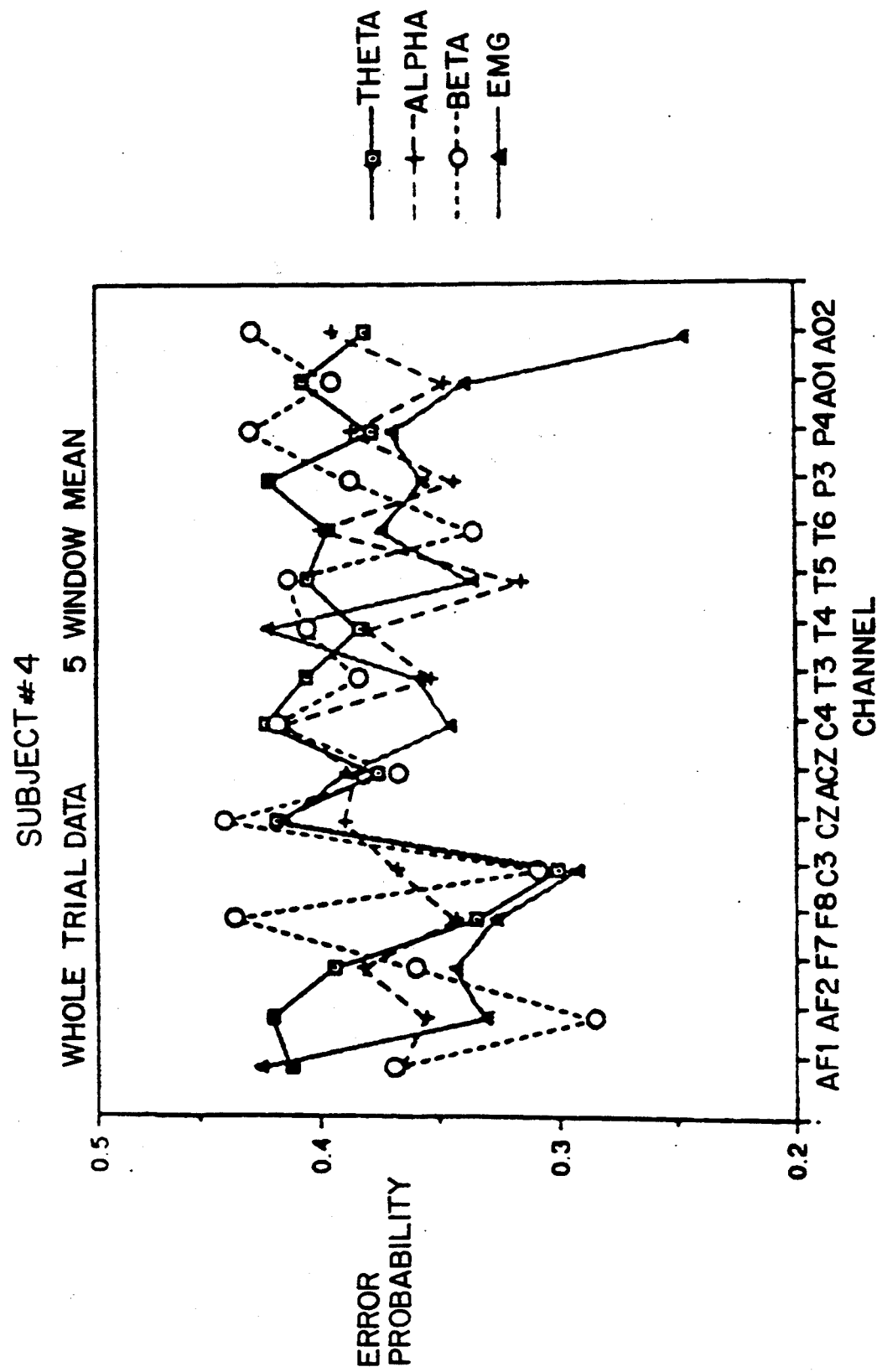

The present invention is illustrated in FIG. 1. As shown therein, a human subject 10, whose head is illustrated, wears a cloth hat 11, or helmet having electrode leads which contact the scalp of the subject. The leads detect the subject's weak analog brain waves and also the electrical activity of their eyes and scalp muscles. Electrodes or other sensors connected by wires to the hat attach to the chest, back, limbs, neck or face to record other physiological signals including heart activity, respiration, facial or limb muscle activity, eye activity, or skin conductance. A suitable EEG hat is described in the inventor's U.S. Pat. No. 5,038,783, issued Aug. 13, 1991 and incorporated by reference herein. The hat has preferably 19–56 independent electrodes, although fewer or more electrodes may be used. The brain waves are amplified, preferably as described in the U.S. Pat. No. 5,038,783, and artifacts detected and removed, for example, as described in U.S. Pat. No. 4,736,751 issued Apr. 12, 1988 and entitled "Brain Wave Source Network Location Scanning Method And System", incorporated by reference herein. Other physiological signals are detected and measured, for example, as follows: Eye movements and blinks are measured with EEG electrodes placed near the eyes, preferably above and below one eye for vertical movements and blinks, and on the nasion and outer cathus of one eye for horizontal movements (electroculogram or EEG). The amplifier response to such eye movements and blinks is similar to that for EEG, except that gain is reduced by a factor of 20 to 50. Alternatively, eye movements and blinks may be measured with an optoelectric device which measures the reflection of infrared light from the margins between the iris and sclera on either side of the pupil. Scalp or facial muscle potentials (electromyogram or EMG) are measured with EEG electrodes placed over scalp muscles or on the face, with a bandpass of from approximately 36 to 100 Hz. Heart activity (electrocardiogram or ECG) is measured with conventional ECG electrodes placed appropriately on the upper chest, limbs or neck. Amplifier response is similar to that for EEG, except that gain is reduced by a factor of 5 to 10. Skin conductance response (SCR) is obtained from the voltage generated by an alternating current of roughly 10 microamps run through two electrodes placed appropriately on the subject's forehead, fingers palm, or armpit. Amplifier response is similar to that for EEG, except that gain is reduced by a factor of 50 to 100. Respiration is measured by a nasal thermistor or an electrically resistive stretch device placed around the upper chest. Changes in resistance are indicated by the amplifier output of a bridge circuit with a regulated voltage input.

In order to use the system, it must first be calibrated to the individual user. This is accomplished when the system is first operated by a particular user. After that, an abbreviated calibration is performed at the start of each session or as needed. During the calibration, simultaneously with the detection of the subject's brain waves and other physiological signals, the user performs a brief battery of standard tasks each with several levels of difficulty. Stimuli for the tasks are presented preferably on the screen 13 of a CRT monitor, or by a loudspeaker 17 connected to the digital computer workstation 12. The subject regards the monitor screen or listens to the loudspeaker and responds using a pressure sensitive switch 12, or alternatively a keyboard 15 or a joystick 16. The tasks, such as those described in patent application Ser. No. 07/766,826, now U.S. Pat. No. 5,295,491, Noninvasive Human Neurocognitive Performance Testing Method and System, incorporated by reference herein, are designed to cause the user to make a graded series of efforts to engage basic neurocognitive functions such as working memory, divided attention, spatial and grammatical reasoning, etc. Visual and auditory stimulus and motor control tasks are also performed.

In addition to the tasks described in U.S. Pat. application Ser. No. 07/766,826, Super-Divided Attention and Working Memory With Binary Response Tasks may be used. The Working Memory With Binary Response Task crosses up to up to four levels of difficulty with two types of information (either the identity or spatial location of a stimulus) to compose a total of eight distinct variants of a simple matching task. Equivalent stimuli are presented and equivalent behavioral responses are required in each condition, with information type and working memory load requirements varying across conditions. Each stimulus item is drawn from a pool 12 capital letters, and stimului are presented once every 4 to 5 seconds. On each trial one of twelve capital letters randomly appears centered at one of 12 positions within a circle. In the two lowest difficulty level conditions the matching task requires comparing either the position or identity of some constant standard stimulus the position or the identity of the current stimulus. The more difficult conditions require comparing the position or identity of the stimulus which occurred on trial (n-x), where x ranges from 1 to 3 trials, with the identity or position of the current (n) stimulus. Thus, these conditions require the subject being tested to mentally update the comparison stimulus on each trial, and to hold either the identity or position of up to 3 stimuli (and their ordering) simultaneously in working memory.

The Super-Divided Attention task requires subjects to perform various combinations of two to five tasks simultaneously, with each task placing demands on a different collection of mental resources, and with overall difficulty level and mental workload increasing with the number of simultaneous tasks. The component subtasks of this test include: (1) a tone discrimination task, where the subject must detect infrequent occurrences of a high pitched tone embedded in a train of low pitched tones; (2) a continuous verbal recognition memory task, where the subject sees a series of common words presented one at a time, and must decide whether the current word is a repetition of a word which appeared a few trials earlier in the series; (3) a Visuomotor Tracking task where the subject must keep a horizontally moving cursor centered in the middle of a screen window by regularly pushing a response button before the moving cursor reaches an endpoint of its movement vector; (4) a dynamic spatial reasoning task in which the subject tracks a moving stimulus on the screen and decides when to initiate the movement of a second stimulus such that the trajectories of the two stimuli will cause them to collide; and, (5) an arithmetic task, in which the sum or difference of two numbers is to be judged higher or lower than a reference number.

For each type of calibration task, the behavioral data are checked on-line to make certain that the apriori difficulty levels do in fact form a graded series for the user at this time. If not, the difficulty of the calibration tasks is adjusted on-line in order to obtain an adequate data sample of workload levels.

The physiological data is first processed to remove artifacts, for example as described in the inventor's U.S. Pat. No. 4,736,751, incorporated by reference herein. Using time segments of the decontaminated data that are 100 milliseconds or more, various parameters are extracted which are specific for each type of physiological signal and, possibly, to individual calibration tasks. For heart activity, the parameter is heart rate. For respiration, the parameter is respiration rate and amplitude. For eye activity, the parameters include but are not limited to eye blink rate and eye blink duration. For scalp or limb muscle activity, the parameter is the root mean square value of the signal from each of the muscle sensors. For brain electrical activity, the parameters include but are not limited to power, peak frequency in delta, theta, alpha and beta bands, coherence in delta, theta, alpha and beta bands and coherence at the peak frequency in each band, between-channel covariance in delta, theta, alpha and beta bands (for example as described in U.S. Pat. No. 4,736,751), wavelet transform coefficients, and coefficients of linear or nonlinear models fit to the brain electrical activity data at each electrode site. Prior to computing these parameters, brain electrical activity may be spatially sharpened using an algorithm described in patent application Ser. No. 07/868,724, "EEG Spatial Enhancement Method And System". Descriptive statistics, mean, variance, skew and kurtosis, are computed for these parameters by using values from several consecutive time segments of data. Using a sliding window of these segments, an updated estimate of the descriptive statistics are obtained every n milliseconds where n is the duration of a time segment. These values are used to estimate the velocity and acceleration of the descriptive statistics. The time resolution of the method is n times the number of segments used in the sliding window. Taken together, all of the described variables constitute the basic set of variables used to construct neurocognitive loading scales.

Subsets of the basic variables are combined using Principal Components analysis to decrease the number and statistical dependence between variables submitted to the neural network pattern analysis algorithm used to form the neurocognitive loading scales. The set of submitted variables can be a combination of Principal Components and any of the basic variables described above. Normalizing transforms are applied to these variables as needed. The final transformation is to compute Z-scores across task difficulty levels.

There are two stages of neural network pattern analysis. In the first stage, generic networks are built for customizing to individual users in the second stage. Generic networks are created from neuroelectric measures, with and without other physiologic measures, derived from a population of subjects who have performed the calibration tasks at two or more difficulty levels. From these data, genetic neural network pattern analyzers are developed to index neurocognitive loading for specific functional brain systems. Neuroelectric data (with and without other physiologic data) elicited during the different task difficulty levels define the discrete mental loads to be distinguished by the neural network pattern analyzers. After transforming each subject's data into Z-score variables as described above, data are pooled across subjects and used in a neural network pattern analysis algorithm such as that described in the study below. The experiment described below describes a special case of the algorithm where the goal was to obtain a binary index for two neurocognitive loading levels. The algorithm is extended to handle more than two levels, and generalized to generate a continuous index of neurocognitive loading. In the latter case, networks are further trained to interpolate between levels and extrapolate beyond the lowest and highest levels. In the process of constructing the networks, the algorithm identifies the best combination of variables for accurately and reliably indexing neurocognitive load. The genetic networks so constructed can be combined into larger genetic networks to give neurocognitive loading indices which combine data from several types of physiological and neuroelectric data, or all can be combined to give an overall index.

To maximize the accuracy and reliability of indexing a user's neurocognitive loadings, genetic networks are adjusted using calibration data. The calibration data is gathered from a small set of tasks specifically designed to adequately calibrate a genetic network. Calibration data are used to adjust a small subset of parameters of the neural network pattern analyzers. The adjustments are made to accomodate the peculiarities of the user's neuroanatomy and neurophysiology; i.e., the particular conductive properties of the user's tissues, geometry of these tissues, neurodynamical properties of the user's brain, and the user's functional brain organization.

The Sympathetic Neurocognitive Adaptive Computer Interface system is then used as follows: As the user is performing a task at the computer, her or his neuroelectric signals, with or without other physiological signals, are measured, artifacts are removed, and the decontaminated signals are processed as described above to derive the final Z-scores used by the neural network pattern analyzers. These Z-scores are fed into each of the customized networks yielding an ongoing measure of neurocognitive loading for each of the major regional brain systems and, using a network that combines the regionally specific networks and, optionally, the networks incorporating information from other physiological signals, an overall measure of neurocognitive workload.

The information about a user's current level of mental effort and activation of major brain systems can be used by the computer system in a variety of ways, depending on the application. For instance, in the case of a user controlling a complex system such as an airplane, the system can take over some of the functions being performed by the user if the overall mental effort score is higher than a critical threshold. Conversely, if the overall score is too low, the system can assign more functions to the user to perform. The system can also adjust the sense modality and form of information presented to the user based on the relative activation of the major regional brain systems. For example, if the user's visual spatial processing areas are too occupied, but the overall mental workload is not too high, the system can change the presentation format of some of the tasks from visual spatial to visual and auditory numeric and verbal. Analogous sorts of application can be made in computer aided instruction applications, or even when a user is passively watching a multimedia presentation, as mentioned above.

The following description is of an experiment demonstrating the use of neural network pattern recognition technology to extract physiological indices which discriminate two levels of mental workload.

METHOD OF EXPERIMENT

Subjects. Four right-handed, male, Air Force fighter test pilots served as subjects. The data reported here were collected as part of a larger, three-day study into the neurophysiological changes associated with prolonged task performance (Gevins et al. 1990). These data were recorded early during the second day of the experiment, before subjects showed subjective, behavioral or neural signs of fatigue. On the first day, the subjects practiced the tasks for about 6 hours, until reaction times and error rams reached asymptote.

Workload Task. Subjects engaged in a continuous performance task in which the level of mental workload was varied while stimulus and response properties were the same. Single digit stimulus numbers were presented on a Videographics-II amber CRT located 70 cm from the subject. Stimulus numbers had an illumination of 11 cd/sq meter against a background of 0.1 cd/sq meter. Subjects were instructed to fixate on the center of the screen and avoid any eye movements during the trial. They were also asked to withold blinking until the intertrial intervals. Each trial began with the disappearance of an "X" from the center of the screen, followed 750 msec later by the appearance of a stimulus number which signaled the subject to respond with graded flexion (0.1–0.9 Kg) of the right index finger against an isometric pressure transducer. In a low-load (LL) condition subjects responded with a force proportional to the latest stimulus number, while in a high-load (HL) subjects had to respond with the force indicated by the "2-back" stimulus number, i.e. the one presented two trials earlier (Gevins et al. 1990). A random 20% of the trials in each task were response-inhibition trials in which no finger response was to be made. In the LL condition these trials were indicated by the stimulus number "0", while in the HL condition no response was required when the current stimulus number matched the 2-back stimulus number. (The number "0" did not occur in the HL condition.) A 2-digit feedback number indicating the force actually applied was presented 1 sec after the response peak, further increasing the difficulty of the HL condition by interfering with a subject's ability to remember the previous two stimulus numbers. Stimulus and feedback numbers subtended a visual angle under 1.5 degrees; they had a duration of 325 msec, and an illumination of 11 cd/sq meter against a background of 0.1 cd/sq meter. In order to keep subjective response production difficulty equivalent across tasks and throughout the session, an adaptive error tolerance (AET) was used. This was the mean error on the previous 5 response trials. If the response error was below the AET, the feedback number was underlined, indicating a "WIN". The subjects performed the two task conditions in separate blocks of 50 trials per block. Subjects performed between 500 and 900 trials of each condition. The mean percentage of responses on response-inhibition trials was 0.4 for the LL and 7.7 for the HL conditions. Based on these performance differences, one can infer that the two conditions in fact differed in mental workload. These performance differences were also consistent with subjects' subjective reports that the HL condition was much more difficult than the LL condition.

Physiological Measurements. The EEG was recorded from 27 scalp electrodes, placed according to an expanded "10-20" System (Gevins et al 1989, 1990) and referenced to the right mastoid. EEG was also recorded from the left mastoid. Bioelectric Systems Model AS-64P amplifiers were used, with maximum amplitude of 140 $\mu v$ peak to peak. The bandpass had a 6 db/oct rolloff below 0.016 Hz and 24 db/oct rolloff above 50 Hz. The EEG was digitized to 11 bits onto magnetic tape at 128 Hz, from 0.75 sec before the stimulus to 1.25 sec after the feedback. Electro-oculogram (EOG) recordings of vertical and horizontal eye movements, and electromyogram (EMG) recordings from the flexor digitorus muscle of the right hand were also obtained. A linked-mastoid reference was computed offline prior to editing. Before further analysis the EEG data were manually reviewed and edited to remove data with head and body movement artifacts, more than a moderate background level of muscle potential contamination, eye movements and blinks, and artifacts due to poor electrode contact, dead or saturated channels. EKG signals were reviewed and edited for EMG and movement contamination. Trials with less than 2 inter-beat intervals (IBIs, time between consecutive R-waves) or with incorrect R-wave detections (the R-wave detection procedure is described below) were excluded.

Data Analysis. Inasmuch as a physiology-based workload measure for use in operational environments will likely need to be calibrated to each individual to achieve optimal sensitivity and reliablity, each subject's data was analyzed independently. The analysis consisted of removing trials containing artifacts, separating the data into training and testing sets, choosing relevant signal features, computing feature values on the training data, examining the distributions of these values to choose a set of candidate features for classifier-directed feature selection and classification analysis (Gevins 1980; Gevins and Morgan 1986), performing these analyses for several candidate feature sets, and validating classification performance using the testing data sets. EKG, EEG and EMG variables were investigated. The instructions to avoid eye movements and blinks during the trials resulted in insufficient eye movement data for us to include this feature in our analysis.

To derive signal features for the EEG data, power spectra were computed for each trial, windowed with a 25% cosine taper. Each trial contained roughly 3-4 seconds of data. We examined average spectra for 16 channels of EEG (see FIG. 2) and chose to derive EEG features for pattern recognition from signal power in standard EEG frequency bands: theta (4 to 7 Hz), alpha (8 to 13 Hz) and beta 1 (14 to 25 Hz). Hanning-windowed FIR filters were used which had 0.5 second impulse response length (6 dB down at the edge frequencies; 17.8 dB/octave rolloff). EEG activity below 4 Hz was excluded since, in many operational contexts, highpass filters with approximately a 4 Hz cut-off would likely be required to reduce or eliminate head and body movement artifacts. Frontal theta was excluded since this signal feature is highly sensitive to small eye blinks and movements. Central theta was excluded so that workload indices would not be based on potentials associated with the control of movement. Scalp EMG features were derived from signal power in the 25-55 Hz range at lateral and frontal peripheral EEG channels. Again, a Hanning-windowed FIR bandpass filter with 0.5 second impulse length was used.

Two signal features were extracted from the EKG data: heart rate (HR) based on the IBI and heart rate variation (HRV) based on root mean square (RMS) differences between successive IBIs. Data were not collected between trials, therefore HR and HRV could only be estimated within trials. Estimates were thus typically based on 3 to 4 IBIs. To measure IBI, R-waves were detected using a weighted average with a 3-5 second time constant for an adaptive baseline offset, and an adaptive threshold based on a slower average of already detected R-peaks. Timing constraints were used to eliminate artifactual IBI estimates (i.e., that were either too short or too long to be physiological). Moderate baseline variation within a trial and moderate EMG bursts were handled well by the detector.

Moving means and variances were computed for all signal features by using windows of In consecutive trials overlapped by n−1 trials (n=5 and n=20 were used). This high degree of overlap corresponds to an updated workload measurement roughly every 3-4 seconds with a time resolution of roughly 3n to 4n seconds. Prior to the windowing operation, trials were separated into training and testing sets by sequentially placing two trials in the training set and one trial in the testing set. This preserved temporal sequencing in each of the two data sets to the degree allowed by eliminating artifact contaminated trials and eliminated the possiblity of statistical dependence between the two data sets that would otherwise result from the windowing operation. Classification results still could have been biased because testing data samples were highly correlated due to the high degree of overlap; hence, as a further precaution, the network classifiers were also tested (not trained) with data computed from successive, non-overlapped windows. This was done only when n was sufficiently small to provide a reasonable number of testing samples; i.e., n=5.

To select features for the neural network classification analysis, a one-dimensional classification error probability was estimated for each candidate mean and variance feature by computing z-scores across workload conditions on the training data, estimating the distributions of these values, and finding a threshold which would result in minimal classification errors. FIG. 3 shows the mean one-dimensional classification error probabilities for each frequency band at each location for all of the subjects, using a 5-trial window. A set of 10 to 20 candidate features with low error probabilities were selected, taking care to ensure an adequate representation of features across scalp locations and frequency bands, and excluding features that might be overly prone to artifact (e.g., frontal theta which is sensitive to tiny eye movements).

EKG and EEG features were first analyzed separately, then in combination. Because the heart rate measures could not be estimated on every trial, no attempt was made to combine EKG with other measures in the pattern recognition analysis. In the EEG analysis, an attempt was made to examine features associated with brain activity in isolation from other factors. Thus several potential features were excluded from these analyses, including: beta-band features from peripheral channels, which are likely to have EMG contamination; frontal and central theta-band features, which are likely to have significant eye and motor control components; and the EMG band (25-55 Hz). In the combined EEG and EMG analysis we relaxed these constraints.

For one subject, Principle Components Analysis (PCA) was necessary to find features with good classification performance in the EEG analysis. PCA features were examined exactly as non-transformed features were examined. In performing the PCA the weights of the original features in the principal components which had low error probabilities were examined. Those that had little influence in this subset of components were excluded and PCA was performed on the remaining features.

A well-proven neural network algorithm was used that iteratively generates and evaluates a two-layered feed-forward neural network from a set of candidate features, automatically identifying small subsets of features that produce the best classification on the data set aside for training (Viglione, 1970; Gevins, 1980; Gevins and Morgan, 1986). In brief, the algorithm first forms all possible combinations of a small number of candidate features out of a larger pool of candidates. These combinations are used to construct candidate neural units to use in the first layer, the "input" layer, of the network. Discriminant analysis is used to determine characteristics of the candidate units. Initially, the candidate unit with the best classification performance is selected and its binary output is weighted and fed into the single, binary output unit of the network. The input unit's weighting and the output unit's threshold are adjusted iteratively to minimize classification error. The algorithm continues to add "input" layer neural units one at a time until a pre-specified limit is reached or an additional unit fails to significantly improve classification accuracy. At each iteration, the algorithm picks the candidate neural unit that maximally improves overall classification performance on the training data. This algorithm was given 10 to 20 candidate variables, was set to use from 1 up to 5 features for the input unit(s), and was restricted to use not more than 3 input units. The upper limits were set so that the number of possible feature combinations was not excessive and, for a network with a single input unit or a network with all input units based on a single feature, the number of training samples exceeded the number of free network parameters by 10. From 58 to 142 trials were available for training.

Results

EKG. Table 1 reports univariate classification accuracy, 100(1-error probability), for data processed using a 20-trial window. Mean HR, HR variance, and mean HR variance are shown. EKG was not recorded for Subject 2. Mean classification performance across EKG-derived features for the three remaining subjects were 63%, 72%, and 70%.

TABLE 1

Classification accuracy of univariate heart rate measures. HRV = heart rate variance. (EKGs were not recorded for subject 2.)

| Subject | Mean HR | HRV | Mean HRV |
|---------|---------|-----|----------|
| 1 | 58% | 71% | 61% |
| 3 | 76% | 62% | 77% |
| 4 | 69% | 69% | 72% |

EEG. Average spectra for 16 of the EEG channels are shown for each subject in FIG. 2. Visual inspection of these plots reveals a large degree of inter-subject variation both in the power level and topographic distribution of the different frequency bands, and in the effect of workload. One common finding across subjects is decreased alpha band power with increased workload. Another trait common to three of the subjects is increased EMG activity in the high workload condition.

Results of neural network pattern analysis are shown in Table 2. High cross-validation classification accuracy was achieved using a 20-trial window length; this translates to a time resolution of roughly 80 seconds. Performance of the simplest neural networks that achieved at least 90% accuracy on the training data are reported. They all had a single input unit using from 1 to 3 features and the number of data samples per network parameter ranged from 19 to 38. Classification accuracy on the testing data for the four subjects were 97%, 100%, 100%, and 92%. The measure of relative feature importance reported in the table is simply the weighting of each feature in the single input unit normalized by the maximum weighting. For Subject 4, for whom principal components were used as input variables to the neural network algorithm, the feature weightings reported are the principal component weightings normalized by the largest weight since only one principal component was needed. Consistent with the inter-subject variation noted above, the most important features for classification were different for each subject. Temporal location theta and/or alpha activity were highly important features for three of the subjects. Occipital theta, frontal alpha, and central beta activity were each highly important for at least one of the subjects.

TABLE 2

Accuracy of classifying EEG features, unconfounded by movement or motorrelated activity, into low or high mental workload levels, using neural network pattern recognition analysis. "var" = variance. For Subject 4, principal components were used as inputs to the neural networks.

| Subject | Accuracy | Features | Relative Weights |
|---|---|---|---|
| 1 | 97% | T5-theta | 1.00 |
|  |  | T3-alpha | 1.00 |
|  |  | A02-theta | 0.54 |
| 2 | 100% | T3-alpha | 1.00 |
|  |  | AF1-alpha | 0.73 |
| 3 | 100% | A01-theta | 1.00 |
| 4 | 92% | C3-beta | 1.00 |
|  |  | T4-theta | 0.86 |
|  |  | A02-alpha-var | 0.53 |
|  |  | ACZ-beta | 0.45 |
|  |  | T4-alpha | 0.38 |
|  |  | P3-beta | 0.37 |
|  |  | F8-alpha | 0.32 |
|  |  | T4-theta-var | 0.29 |

Combined EEG and EMG.

Results of neural network pattern analysis are shown in Table 3. High cross-validation classification accuracy was achieved using a 5-trial window length; this translates to a time resolution of roughly 20 seconds. As for the study using only EEG variables, the simplest neural networks that achieved at least 90% accuracy on the training data consisted of a single input unit; 1 to 4 features were used and the number of data samples per network parameter ranged from 14 to 25. Classification accuracy on the testing data for the four subjects were 95%, 95%, 99%, and 94%. Since classification results could have been positively biased because data samples in the testing data were highly correlated due to the high degree of overlap between windows, the networks were also tested with features computed with non-overlapped windows. Similar accuracies were achieved for these tests: 92%, 94%, 100%, and 94%. As in the EEG index, there were individual differences in the features used for discrimination. EMG features were highly important for three of the subjects. For Subject two temporal and frontal alpha were the most important features.

TABLE 3

Accuracy of classifying combined EEG and EMG features into low or high mental workload levels, using neural network pattern recognition analysis.

| Subject | Accuracy | Features | Relative Weights |
|---|---|---|---|
| 1 | 95% | A01-emg | 1.00 |
|  |  | A02-beta | 0.66 |
|  |  | P3-emg | 0.32 |
|  |  | C2-beta | 0.1 |
| 2 | 95% | T3-alpha | 1.00 |
|  |  | F7-alpha | 0.31 |
|  |  | F8-emg | 0.29 |
|  |  | AF1-alpha | 0.16 |
| 3 | 99% | F8-emg | 1.00 |
|  |  | A01-emg | 0.80 |
|  |  | AF1-beta | 0.42 |
| 4 | 94% | A02-emg | 1.00 |
|  |  | AF2-beta | 0.67 |
|  |  | T5-emg | 0.54 |

Discussion

The results from this study demonstrate the feasibility of using neural network pattern recognition analysis of subject-specific physiological features to distinguish between levels of mental workload unconfounded by such factors as differences between conditions in the amount of eye or motor activity. These results are thus consistent with prior results from our laboratory in which a neural network pattern recognition analysis was used to detect electrophysiological changes related to variations in mental fatigue or vigilance levels (Gevins et al, 1990), in performance accuracy, and in type of cognitive task being performed.

The most important result to emerge from this work is that multiple spectral features of ongoing EEG and EMG can be used to differentiate physiological patterns associated with high and low levels of mental workload with a temporal resolution of less than thirty seconds. Further, the analysis was performed on overlapped sets of trials, which is akin to using a sliding window of data to obtain a continuous estimate of workload, where, within the window, portions of the signal may not be used due to response contamination. This has the important benefit of allowing the assessment of mental workload even during periods in which some of the signals cannot be used due to artifacts; a situation likely to occur when recordings are made in demanding operational environments. These results also highlight the utility of including multiple physiological measures to more sensitively detect workload variations, as well as the utility of tailoring pattern detectors to the idiosyncracies of individual subjects. These issue are considered at more length below.

Improved Classification with Multiple Features and Classification-Directed Feature Selection. The neural network analysis was applied to physiological features alone or in combination and resulted in very simple networks. In all but one case, multiple signal features were required to distinguish the two mental workload conditions. This is not surprising since the task used requires multiple mental resources, such as stimulus recognition, working memory, and motor preparation and control, and the mapping between these and electrophysiological measurements is likely to be quite complex. By contrast, it was surprising that simple networks having only one input unit were sufficient. This result suggests that, with appropriate candidate signal features, the process of selecting the best combination of features based on classifier performance was the most important aspect of the algorithm that was used rather than the power of neural network structures for handling classification problems (Gevins and Morgan, 1986).

The finding that heartrate is not a sensitive index of mental workload in the current situation may be interpreted as indicating that whereas heartrate may be a useful index for physical workload and emotional stress, it is relatively insensitive to variations in cognitive load per se. In contrast, clean EEG features (i.e. those from which possible contamination due to low frequency motor potentials or high frequency muscle activity were eliminated) showed a high classification accuracy, with a time resolution of 80 seconds. Whereas the exact spatial topographies of EEG features which discriminated between workload levels differed across subjects, these features most often involved changes in alpha and/or theta activity (one of the four subjects presented a more complex picture involving all of the analyzed EEG frequency bands to some extent). These results are consistent with other studies demonstrating spatially distributed changes in alpha and theta band activity as tasks vary in cognitive load. In addition to changes in these spectral bands, several recent studies have also shown that sustained slow potential shifts are reliably related to task difficulty or information load. Given that the current study focused on electrophysiological features which could be reliably recorded in operational environments, and that movement artifacts could potentially be mistaken for slow potential shifts, low frequency features were not included in the formal pattern recognition analyses. Even so, it is worthwhile to note that post hoc examination revealed substantial task-related changes in delta band activity for some of the subjects in this study.

Finally, combining EEG and EMG features again resulted in high classification rates but with a much better time resolution, 20 seconds. Although the relative weighting of EMG features differed across subjects, it was an important factor for all. Whereas high classification rates with good time resolution were obtained here by combining only EMG and EEG measures, the addition of other variables such as EKG, respiration and eye activity may prove valuable.

Individual Differences in Workload Sensitive Electrophysiological Features. The results from this study clearly indicate the need to "calibrate" EEG based workload indices based to the idiosyncracies of individual subjects. Although some general effects were found across subjects, such as a decrease in alpha and increase in EMG activity with higher workload, the fine details of the index structure were highly specific to each subject. Such between-subject variability is not surprising given that all cognitive tasks draw upon several neural subsystems, from those subserving sensory perception, through those underlying stimulus evaluation and decision, to those serving response execution. All these systems are influenced by the subject's abilities and prior experience. Subjects are also likely to use different mental strategies to perform the tasks, and these strategies may change over time with task repetition in a different manner for different subjects. Clearly there are many sources from which the individual differences in the electrophysiological patterns could arise. Yet despite the wide variation across subjects, sophisticated analysis techniques which are calibrated upon each individual's data, can find common factors of mental workload even though the particular pattern of expression may differ considerably across subjects.

It seems likely that a maximally sensitive workload index based on electrophysiological measures might also need to be optimized for different types of tasks. The high classification rates we achieved in both the EEG analysis and the combined EEG and EMG analysis support the view that mental workload can be indexed in several ways. The best method may depend on many factors including the spectral regions in which clean signals are available, the cognitive and motor demands of the task, and the generalizability and sensitivity of the index within these contexts. The results reported here illustrate one of the trade-offs that must be considered when designing a generalized mental workload index. EEG data from which the effects of muscle and motor-related activity were removed were analyzed, since it was assumed that such an index, which is sensitive to a broad spectrum of higher cognitive functions, would be more likely to generalize across tasks than would one which is influenced by idiosyncratic perceptual and motor demands of the tasks. Although EEG features were found which distinguished the two workload levels, the time resolution was fourfold smaller than that achieved when EMG features were included. The best practical solution may be a combination of indices, weighted differentially according to situation-specific demands.

Conclusions. This study illustrates the feasibility of employing neural network-based pattern recognition techniques to combinations of physiological features in order to derive sensitive and reliable inferences about the mental workload of individual subjects. Physiological data can be continuously and unobtrusively recorded while users perform their duties. The combination of the specific features used to assess mental workload can be adjusted on an individual basis to determine the most sensitive index for each person. The combination of several measures and the use of overlapped trials in data analysis reduces the detrimental effect of artifacts, and most importantly, changes in workload levels can be discriminated with good temporal resolution.

REFERENCES

Gevins, A. S. (1980) Pattern recognition of brain electrical potentials. *IEEE Trans. Patt. Anal. Mach. Intell.*, PAMI-2 (5), pp. 383–404.

Gevins, A. S., Bressler, S. L., Cutillo, B. A., Illes, J., Miller, J., Stern, J., Jex, H. (1990) Effects of prolonged mental work on functional brain topography. *EEG clin. Neurophysiol.*

Gevins, A. S., Bressler, S. L., Morgan, N. H., Cutillo, B. A., White, R. M., Greer, D. & Illes, J. (1989) Event-related covariances during a bimanual visuomotor task. Part II. v.ul Electroencephalogr. clin. Neurophys., 74(2) 147–160.

Gevins, A. S. and Morgan, N. H. (1986) Classifier-directed signal processing in brain research. *IEEE Trans. Biomed. Eng.*, BME-33 (12), pp. 1054–1068.

Viglione, S. S. (1970), "Applications of pattern recognition technology," In: J. M. Mendel & K. S. Fu, *Adaptive Learning and Pattern Recognition Systems*, New York: Academic Press.

I claim:

1. A method in human-computer interface for the computer to automatically react to the user's neurocognitive workload without the user exerting muscle command action, by the computer changing a portion of a program being run by a computer; including the steps of:

(a) presenting the user with a battery of standard tasks and, while the user performs the tasks, detecting and analyzing the brain waves of the user with an EEG (electroencephalograph) device having a plurality of electrodes removably connected to the scalp of the user to determine a normative neurocognitive workload calibration function for the user while the user performs the tasks, and recording the normative neurocognitive calibration function in the computer system memory;

(b) the user operates the computer system using the computer system muscle operated input control means;

(c) simultaneously with (b) detecting and analyzing the brain waves of the user with an EEG (electroencephalograph) device having a plurality of electrodes removably connected to the scalp of the user, to determine on-line neurocognitive workload score from the user's normative neurocognitive calibration function; and (d) adjusting a portion of the program being run by the computer system if the user's on-line neurocognitive workload score is a predetermined amount below or above a threshold value.

2. A method as in claim 1 and simultaneouly with (a) and (c) detecting and measuring other physiological signals of the user selected from the group of facial muscle, eye muscle, heart activity and respiration.

3. A method as in claim 1 wherein the workload calibration function of (a) includes the overall normative neurocognitive workload function and the workload score of (c) includes the overall on-line neurocognitive workload score.

4. A method as in claim 1 wherein the neurocognitive workload function of (a) includes neurocognitive workload functions for each of a plurality of specialized brain systems and the neurocognitive workload score of (c) includes a score for each of the specialized brain systems.

5. A method as in claim 1 wherein in (a) the workload calibration function is determined using a neural network pattern analyzer in which generic networks are created derived from a normal population performing the standard tasks.

6. A method as in claim 5 wherein a specific calibration function is obtained for each user in (a) by transforming each user's brain wave data to Z-score variables and inputting the Z-score variables into the neural network pattern analyzer.

7. A method as in claim 1 wherein the user in steps (a) and (c) wears a hat having a plurality of electrodes to contact the scalp of the user.

8. A method as in claim 1 wherein the computer is a portion of a computer-aided instruction system.

9. A method as in claim 8 wherein the portion of the program is adjusted to a less difficult instruction level if the user's neurocognitive workload score is above a threshold value.

10. A method as in claim 8 wherein the portion of the program is adjusted to a more difficult level if the user's neurocognitive workload score is below a threshold value.

11. A method as in claim 8 wherein the portion of the program being run is changed depending on the user's use of specialized brain systems involved with perception, action, and cognition which include: the planum temporale, superior temporal gyrus, Heschl's gyrus and associated structures involved with auditory processing and speech perception; the occipital and inferotemporal cortices and the parieto-occipito-temporal junction and associated structures involved in visual processing and pattern recognition; the precentral gyrus, lateral premotor cortex, supplementary motor cortex, and associated structures involved with the planning, initiation, and execution of motor movements; the dominant hemisphere frontal operculum, dorsalateral frontal cortex, and planum temporale and supramarginal gyrus and associated structures involved with language functions; and the networks of structures encompassing the prefrontal, parietal, and temporal association cortices and associated regions involved in processing spatial information, in preparation and sequential planning, in reasoning, in focusing and shifting attention, in learning, and in working memory.

12. A method as in claim 1 wherein the computer is part of a computer based controlled system.

13. A method as in claim 12 and including the step of the computer based controlled system reacting to the user's neurocognitive workload score being above a threshold by a predetermined amount, the computer adjusting a portion of the program so that the user is presented with less-demanding tasks.

14. A method as in claim 12 and including the step of the computer based controlled system reacting to the user's neurocognitive workload score being below the threshold by a predetermined amount by the computer adjusting a portion of the program so that the user is presented with more-demanding tasks.

15. A method as in claim 12 and including the step of the computer based controlled system reacting to the user's use of regional brain systems involved with perception, action, and cognition which include: the planum temporale, superior temporal gyrus, Heschl's gyrus and associated structures involved with auditory processing and speech perception; the occipital and inferotemporal cortices and the parieto-occipito-temporal junction and associated structures involved in visual processing and pattern recognition; the precentral gyrus, lateral premotor cortex, supplementary motor cortex, and associated structures involved with the planning, initiation, and execution of motor movements; the dominant hemisphere frontal operculum, dorsalateral frontal cortex, and planum temporale and supramarginal gyrus and associated structures involved with language functions; and the networks of structures encompassing the prefrontal, parietal, and temporal association cortices and associated regions involved in processing spatial information, in preparation and sequential planning, in reasoning, in focusing and shifting attention, in learning, and in working memory.

16. A system in human-computer interface including a computer which runs a plurality of programs and which automatically reacts to the user's neurocognitive workload without the user exerting muscle command action by the computer changing a portion of the program being run by a computer, including:
(a) means for presenting the user with a battery of standard tasks; means for detecting and analyzing the brain waves of the user comprising an EEG (electroencephalograph) device having a plurality of electrodes adapted to be removably connected to the scalp of the user to determine a normative neurocognitive workload calibration function for the user while the user performs the tasks and means for recording the normative neurocognitive calibration function comprising a portion of computer memory;
(b) muscle operated input control means to operate the computer;
(c) means for simultaneously with the operation of (b) to detect and analyze the brain waves of the user comprising said EEG device to determine on-line neurocognitive workload scores from the user's normative neurocognitive calibration function; and
(d) means to adjust a portion of the program being run by the computer if the user's on-line neurocognitive workload score is a predetermined amount below or above a threshold.

17. A system as in claim 16 and means for simultaneouly with (a) and (c) detecting and measuring other physiological signals of the user selected from the group of facial muscle, eye muscle, heart activity and respiration.

18. A system as in claim 16 wherein the workload calibration function of (a) includes the overall normative neurocognitive workload function and the workload score of (c) includes the overall on-line neurocognitive workload score.

19. A system as in claim 16 wherein the neurocognitive workload function of (a) includes neurocognitive workload functions for each of a plurality of specialized brain systems and the neurocognitive workload score of (c) includes a score for each of the specialized brain systems.

20. A system as in claim 16 and including a neural network pattern analyzer in which generic networks are created derived from a normal population performing the standard tasks.

21. A system as in claim 20 and including means for obtaining a specific calibration for each user in (a) by transforming each user's brain wave data to Z-score variables and inputting the Z-score variables into the neural network pattern analyzer.

22. A system as in claim 16 and including a hat having a plurality of electrodes to contact the scalp of the user.

23. A system as in claim 16 wherein the computer is a portion of a computer-aided instruction system.

24. A system as in claim 23 wherein the portion of the program is adjusted to a less difficult instruction level if the user's neurocognitive workload score is above a threshold.

25. A system as in claim 23 wherein the portion of the program is adjusted to a more difficult level of the user's neurocognitive workload score is below a threshold.

26. A system as in claim 23 wherein the portion of the program being run is changed depending on the user's use of regional brain systems involved with perception, action, and cognition which include: the planum temporale, superior temporal gyrus, Heschl's gyrus and associated structures involved with auditory processing and speech perception; the occipital and inferotemporal cortices and the parieto-occipito-temporal junction and associated structures involved in visual processing and pattern recognition; the precentral gyrus, lateral premotor cortex, supplementary motor cortex, and associated structures involved with the planning, initiation, and execution of motor movements; the dominant hemisphere frontal operculum, dorsalateral frontal cortex, and planum temporale and supramarginal gyrus and associated structures involved with language functions; and the networks of structures encompassing the prefrontal, parietal, and temporal association cortices and associated regions involved in processing spatial information, in preparation and sequential planning, in reasoning, in focusing and shifting attention, in learning, and in working memory.

27. A system as in claim 16 wherein the computer is part of a computer based controlled system.

28. A system as in claim 27 and including means for the computer-based controlled system to react to the user's neurocognitive workload score being above a threshold by the computer adjusting a portion of the program so that the user is presented with less-demanding tasks.

29. A system as in claim 27 and including means for the computer based controlled system to react to the user's neurocognitive workload score being below a threshold by the computer adjusting a portion of the program so that the user is presented with more-demanding tasks.

30. A system as in claim 27 and including means for the computer based controlled system to react to the user's use of regional brain systems involved with perception, action, and cognition which include: the planum temporale, superior temporal gyrus, Heschl's gyrus and associated structures involved with auditory processing and speech perception; the occipital and inferotemporal cortices and the parieto-occipito-temporal junction and associated structures involved in visual processing and pattern recognition; the precentral gyrus, lateral premotor cortex, supplementary motor cortex, and associated structures involved with the planning, initiation, and execution of motor movements; the dominant hemisphere frontal operculum, dorsalateral frontal cortex, and planum temporale and supramarginal gyrus and associated structures involved with language functions; and the networks of structures encompassing the prefrontal, parietal, and temporal association cortices and associated regions involved in processing spatial information, in preparation and sequential planning, in reasoning, in focusing and shifting attention, in learning, and in working memory.

* * * * *